United States Patent
Grossschmidt et al.

(10) Patent No.: US 8,801,814 B2
(45) Date of Patent: Aug. 12, 2014

(54) PROCESS AND APPARATUS FOR THERMAL PARTIAL OXIDATION OF HYDROCARBONS

(75) Inventors: Dirk Grossschmidt, Mannheim (DE); Maximilian Vicari, Limburgerhof (DE); Christian Weichert, Bad Duerkheim (DE); Hans Zapf, Mutterstadt (DE); Andreas Joa, Neustadt (DE); Ravindra Aglave, Mannheim (DE); Jens Denecke, Speyer (DE)

(73) Assignee: BASF SE, Ludwigshafen (DE)

( * ) Notice: Subject to any disclaimer, the term of this patent is extended or adjusted under 35 U.S.C. 154(b) by 885 days.

(21) Appl. No.: 12/918,942

(22) PCT Filed: Feb. 20, 2009

(86) PCT No.: PCT/EP2009/052052
§ 371 (c)(1),
(2), (4) Date: Aug. 23, 2010

(87) PCT Pub. No.: WO2009/109473
PCT Pub. Date: Sep. 11, 2009

(65) Prior Publication Data
US 2011/0016790 A1    Jan. 27, 2011

(30) Foreign Application Priority Data
Mar. 5, 2008   (EP) .................................... 08152302

(51) Int. Cl.
*C10J 3/46*   (2006.01)

(52) U.S. Cl.
USPC ........... 48/197 R; 48/127.1; 48/127.9; 48/61; 48/127.5; 48/198.8; 48/198.1; 48/212; 48/213; 48/216; 422/224; 422/229

(58) Field of Classification Search
USPC .......................... 48/61, 127.9, 127.1, 197 R
See application file for complete search history.

(56) References Cited

U.S. PATENT DOCUMENTS

| 1,435,778 | A | * | 11/1922 | Williams | ...................... 239/139 |
| 2,179,378 | A | | 11/1939 | Metzger | |
| 2,813,138 | A | | 11/1957 | MacQueen | |

(Continued)

FOREIGN PATENT DOCUMENTS

| DE | 875 198 | 3/1953 |
| DE | 1 051 845 | 3/1959 |

(Continued)

OTHER PUBLICATIONS

U.S. Appl. No. 12/675,187, filed Feb. 25, 2010, Olbert, et al.

(Continued)

*Primary Examiner* — Kaity Handal
(74) *Attorney, Agent, or Firm* — Oblon, Spivak, McClelland, Maier & Neustadt, L.L.P.

(57) ABSTRACT

A process for partial oxidation of hydrocarbons in a reactor, in which a stream comprising the hydrocarbon and a stream comprising the oxygen are fed to the reactor, wherein both streams fed to the reactor are conducted within the reactor separately through in each case one or more spatially separate lines, these lines having turbulence generators in their interior, owing to which, as a result of the imposed deflection of the flow direction downstream of turbulence generators, a highly turbulent flow field forms, and the streams are then mixed in a mixing zone after exiting from the lines and then converted in a reaction zone.

15 Claims, 4 Drawing Sheets

(56) References Cited

U.S. PATENT DOCUMENTS

| | | | |
|---|---|---|---|
| 3,081,818 A | | 3/1963 | Braconier et al. |
| 3,256,066 A | * | 6/1966 | Higgins ................ 422/151 |
| 3,399,245 A | * | 8/1968 | Knapp ................... 585/540 |
| 3,726,634 A | * | 4/1973 | Thomson et al. ......... 431/353 |
| 3,847,564 A | * | 11/1974 | Marion et al. ............. 48/95 |
| 5,789,644 A | | 8/1998 | Paessler et al. |
| 6,319,458 B1 | * | 11/2001 | Jung et al. ............... 266/266 |
| 7,108,838 B2 | * | 9/2006 | McGee .................... 422/224 |
| 7,727,495 B2 | * | 6/2010 | Burd et al. ............... 422/312 |
| 2008/0188698 A1 | | 8/2008 | Bartenbach et al. |
| 2009/0123882 A1 | * | 5/2009 | Eroglu et al. ................ 431/8 |
| 2010/0175379 A1 | * | 7/2010 | Liu et al. .................. 60/723 |

FOREIGN PATENT DOCUMENTS

| | | |
|---|---|---|
| DE | 1 057 094 | 5/1959 |
| DE | 44 22 815 | 1/1996 |
| DE | 10 2005 018981 | 10/2006 |
| DE | 10 2009 001 045 A1 | 9/2009 |
| GB | 818 395 | 8/1959 |
| GB | 824 328 | 11/1959 |
| GB | 958 061 | 5/1964 |

OTHER PUBLICATIONS

U.S. Appl. No. 12/675,137, filed Feb. 25, 2010, Olbert, et al.

* cited by examiner

PROCESS AND APPARATUS FOR THERMAL PARTIAL OXIDATION OF HYDROCARBONS

BACKGROUND OF THE INVENTION

The present invention relates to an improved process for partial oxidation of hydrocarbons in a reactor, in which a stream comprising the hydrocarbon and a stream comprising the oxygen are fed to the reactor, and to an apparatus for performing the process according to the invention.

High temperature reactions for partial oxidation of hydrocarbons are typically carried out in a reactor system comprising mixing unit, burner and quench.

One example of such a partial oxidation in the high temperature range is the preparation of acetylene and synthesis gas by partial oxidation of hydrocarbons. This is described, for example, in DE 875198, DE 1051845, DE1057094 and DE 4422815.

These explain the mixer/burner/firing chamber/quench combinations typically used for the BASF-Sachsse-Bartholomé acetylene process—referred to hereinafter, when reference is made to the combination, simply as "reactor".

The natural gas and oxygen starting materials are heated separately, typically up to very close to 700° C. The reactants are mixed intensively in a mixing zone and, after they pass through a burner block, reacted. In these cases, the burner block consists of a particular number of parallel channels in which the flow rate of the ignitable oxygen/natural gas mixture is higher than the flame speed (reaction speed, conversion speed), in order to prevent the flame from penetrating into the mixing chamber. The metallic burner block is cooled in order to withstand the thermal stresses. According to the residence time in the mixing chamber, there arises the risk of premature ignition and flashback owing to the limited thermal stability of the mixtures. Here, the term "ignition delay time" or "induction time" is used to mean the time span within which an ignitable mixture does not undergo any significant intrinsic thermal change. The induction time depends on the type of hydrocarbons used, the mixing state, and on pressure and temperature. It determines the maximum residence time of the reactants in the mixing chamber. Reactants such as hydrogen, liquefied gas or light petroleum, whose use is particularly desirable in the synthesis process owing to yield and/or capacity increases, are notable for a comparatively high reactivity and hence short induction time.

The acetylene burners used on the modern production scale are notable for their cylindrical geometry of the firing chamber (reactor). The burner block preferably has hexagonally arranged passage bores. In one embodiment, for example, 127 bores of internal diameter 27 mm are arranged hexagonally on a circular base cross section with diameter approx. 500 mm. In general, the channel diameters used are from about 19 to 27 mm in diameter. The downstream firing chamber in which the flame of the acetylene-forming partial oxidation reaction is stabilized is likewise of cylindrical cross section and corresponds in terms of appearance to that of a short tube (of, for example, diameter 533 mm and length 400 mm). The entire burner composed of burner block and firing chamber is hung into a quench vessel of larger cross section by means of a flange from the top. At the height of the exit level from the firing chamber, quench nozzles are installed outside its circumference on one or more quench distributor rings which atomize the quench medium, for example water or oil, with or without the aid of an atomization medium and spray it in approximately at right angles to the main flow direction of the reaction gases leaving the firing chamber. This direct quench has the task of cooling the stream extremely rapidly as it reacts, such that subsequent reactions, i.e. more particularly the degradation of acetylene formed, are frozen. The range and distribution of the quench jets are ideally such that a very homogeneous temperature distribution is achieved within a very short time.

The stabilization of the flame within the burner in which the chemical reaction takes place (referred to hereinafter as reaction zone) is of high significance for the effectiveness and economic viability of the process. The flame stabilization is based in the known burner system described above on two mechanisms whose simultaneous employment is required. As well as a stabilizing flame, there is also accumulation body stabilization owing to recirculated hot gas.

The acetylene burners used on the current production scale are notable for a cylindrical geometry of the firing chamber. The feed stocks are premixed by means of a diffuser and, avoiding backmixing, fed to the burner block via hexagonally arranged passage bores. In the known processes, the feed stocks are premixed in the mixing diffuser in a relatively large volume and with high preheating temperatures. According to the capacity of the burner, the mixing diffuser is notable for a design in which the residence time of the reactants and their induction times are within the same order of magnitude. Owing to an elevated proportion of reactive feedstock components, catalytically active particles and surfaces, for example coke, rust, etc., it may occur that the induction times for the ignition of the mixture are exceeded.

These premature ignitions lead to operation shutdowns and hence to a lowering of the effectiveness and economic viability of the process.

DE 10 2005 018 981 A1 or U.S. Pat. No. 2,179,378 describe apparatus which shift the introduction of the reactant streams to a small space in the immediate vicinity of the burner block bores. The burner block bores thus serve as mixing tubes in which the reactant mixture is formed. A suitable configuration of the mixing geometry achieves high speeds, which prevent back-ignition of the flame into the burner block bores and simultaneously ensure rapid mixture formation.

The implementation of this design is associated with a considerable level of construction complexity, since homogeneous distribution of the reactant streams into suitable mixing units distributed over all burner block bores has to be ensured. In addition, there is the risk of flashback into the individual mixing tubes and of stabilization of the flame within the stoichiometric range of the mixing field. This is true in the case of inhomogeneity of the reaction mixture, in which case the flow rate in the mixing tube falls into the order of magnitude of the conversion rate.

It is an object of the invention to find an improved process for partial oxidation of hydrocarbons, which avoids the disadvantages mentioned and which, in a simple manner in process technology terms, enables rapid and good mixing of the reactants in a very small space and with short residence times.

Figure 1:
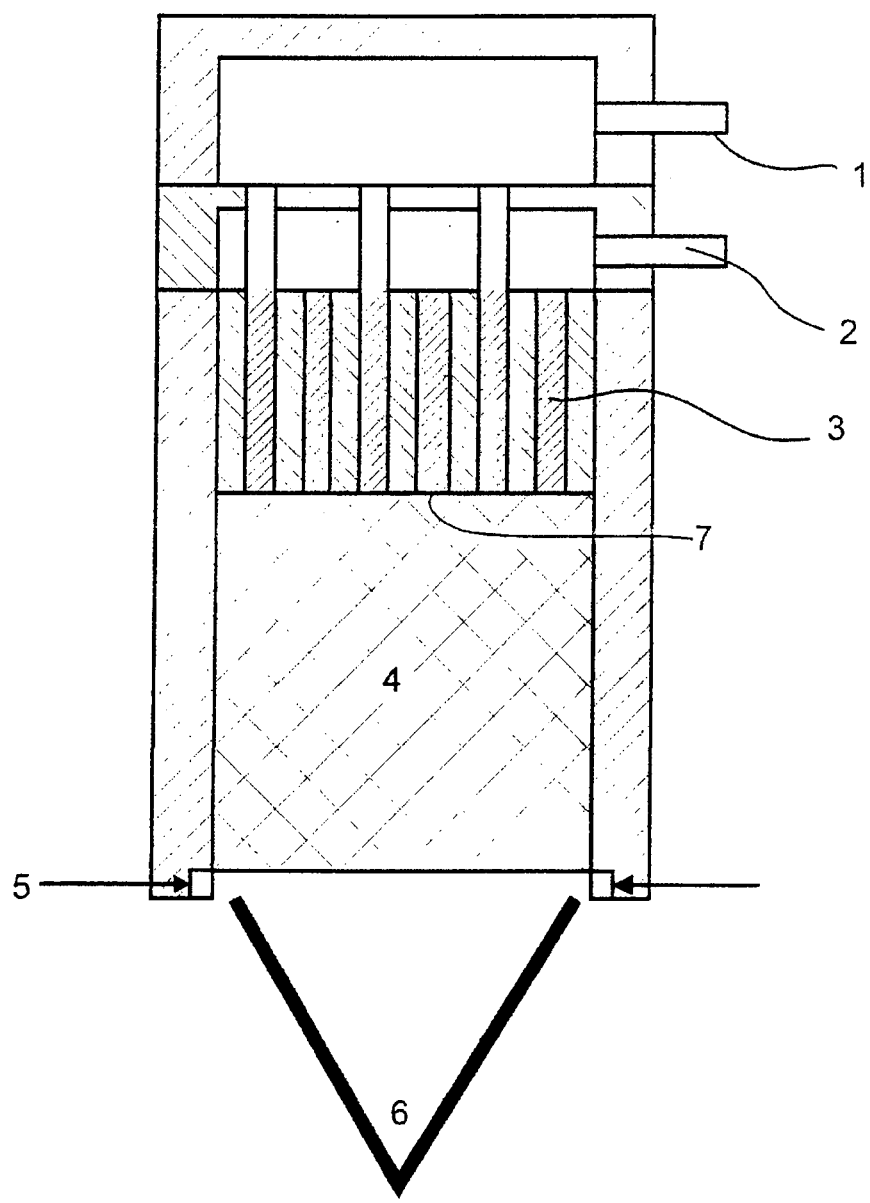
FIG. 1 shows a schematic diagram of an apparatus according to one embodiment of the invention.

Accordingly, a process has been found for partial oxidation of hydrocarbons in a reactor, in which a stream comprising the hydrocarbon and a stream comprising the oxygen are fed to the reactor, wherein both streams fed to the reactor are conducted within the reactor separately through in each case one or more spatially separate lines, these lines having turbulence generators in their interior, owing to which, as a result of the imposed deflection of the flow direction downstream of said turbulence generators, a highly turbulent flow field forms, and the streams are then mixed in a mixing zone after exiting from the lines and then converted in a reaction zone.

In the process according to the invention, the reactant streams are conducted spatially separately from one another in preferably parallel bores, a very high turbulence structure being imparted to the flow therein by turbulence generators. Downstream of the turbulence generators, a mixture of oxidant and fuel is then formed in a very narrow space, the degree of mixing depending on the mixing length, the degree of turbulence and the direction of rotation of the turbulence generator in the bores. The mixing zone is followed immediately by the reaction zone which is stabilized by injection of pilot oxygen into the highly turbulent flow zone.

This sequential arrangement of mixing and reaction space ensures a simple flow regime, which is advantageously not disrupted by further internals.

The process according to the invention offers the possibility of preventing operation shutdowns and outages caused by premature ignition. In addition, it opens up possibilities of partial use of fuels with low induction times, such as synthesis gases or higher hydrocarbons (for example ethane, ethylene or evaporated liquefied gases).

In the process according to the invention, internals referred to as turbulence generators are used in the channels of the burner block. In terms of geometry, the turbulence generators are configured such that they block significant portions of the channel cross section in the installed state and the gas flow in the interior of the channels is passed only through continuous bores present in the turbulence generators. In this context, the channel cross section is understood to mean the area available for the gas to flow through the channel.

In the case of the burner block channels usually formed with a circular cross section, a turbulence generator thus preferably has the shape of a cylinder whose diameter is such that it approaches the circumferential edges of this cylindrical body in the installed state for the blockage of the gas flow explained above, since the external diameter of the cylinder corresponds approximately to the internal diameter of the channel, thus virtually completely suppressing flow of the gas through at the gap which is at most still present to a very small degree. The quality of the seal is determined here especially by the complexity of the manufacture and can additionally be enhanced by further measures known to those skilled in the art.

The height of the cylindrical body used is typically approximately within a range from 1 to 4 channel diameters, preferably from about 2 to 3 channel diameters. Generally, it is advisable in the process according to the invention to configure the turbulence generators in terms of their geometry such that from about 20 to 100% of the length of the burner channel is essentially blocked in accordance with the invention.

The bores introduced into the turbulence generator in accordance with the invention in the installed state essentially do not run or preferably do not at all run parallel to the longitudinal axis of the burner channel. In a preferred embodiment, in the case of the cylindrical body detailed above, it is provided with bores with a slope of from about 80° to 40°, preferably from 60° to 45°. The slope is understood to mean the angle between the longitudinal axis of the cylinder (height axis) and the longitudinal axis of the bore. In the case of axial alignment of the bores in the turbulence generator, this slope would be 0°. This bore is preferably started at the upper or lower circular face of the cylinder close to or at the circumference and then runs with a preferably constant slope in a spiral manner to the opposite circular face. It is advisable to provide the turbulence generator with several bores; typically from about 1 to 6 and preferably 4 bores are selected here.

In the installed state, the turbulence generators thus configured have the effect that the gas necessarily flows through the bores. At the same time, the gas, owing to the slope of the bores, flows in the shape of the aforementioned spiral motion. The direction of motion may thus still be composed firstly of a component in the direction of the longitudinal axis, but, on the other hand, a peripheral component (depending on the point at which the bore starts, for example, according to the circle formed by the diameter of the cylinder) is superimposed on this direction. By the time the gas has flowed through the entire turbulence generator, it has undergone a curved deflection in a circumference angle of from about 45° to 360°, preferably from 90° to 180°. The circumference angle is understood here to mean the total section of the circular arc given by the cylinder geometry which has been covered. The deflection may either be clockwise or counterclockwise.

Figure 4:
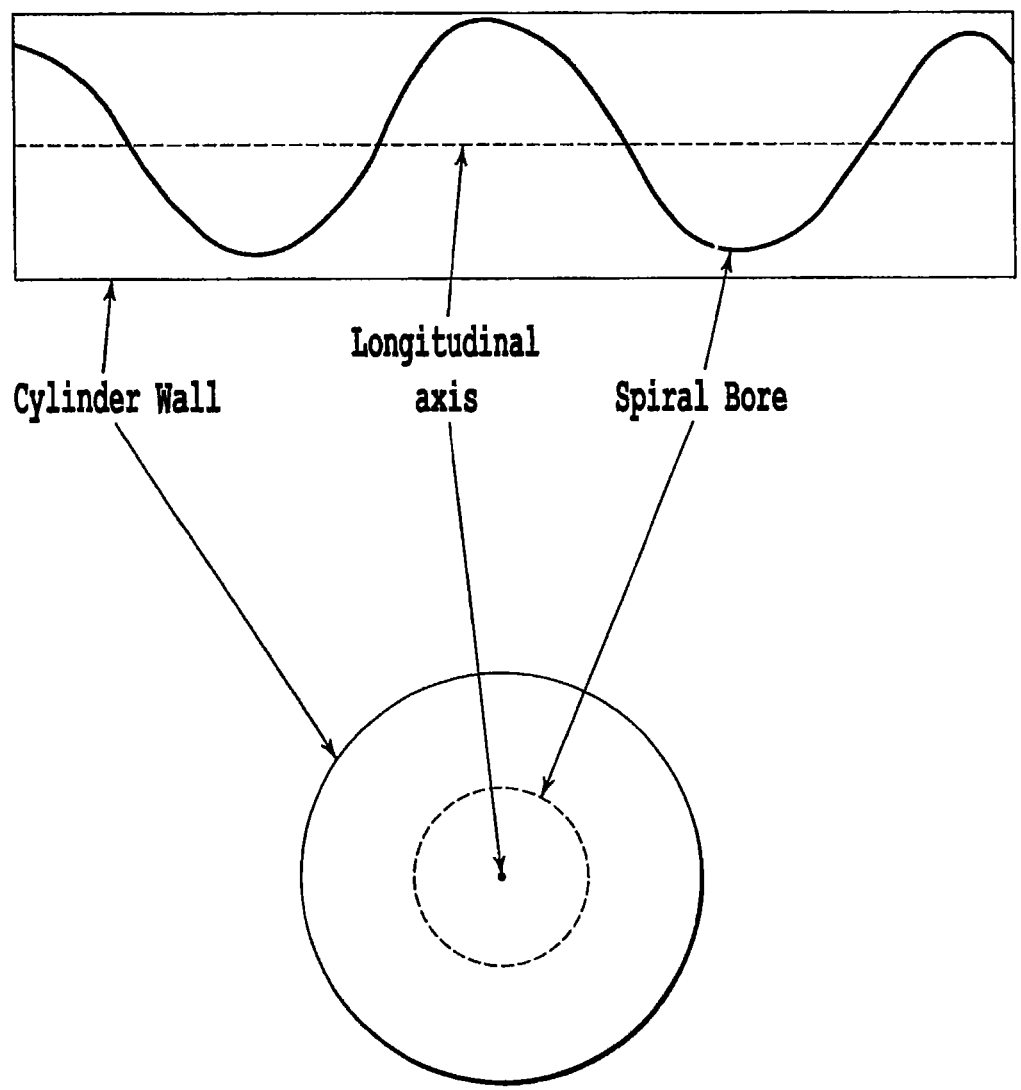
FIG. 4 shows a schematic diagram of the bore in a cylindrical turbulence generator according to one embodiment of the invention.

The structure of a turbulence generator is schematically shown in FIG. 4.

In a preferred embodiment, the turbulence generators block a percentage area of the channel cross section of from about 10% to 70%, preferably from 20% to 50%. The external geometry of the turbulence generators used in accordance with the invention is determined to a significant degree by the geometry of the burner channel. In the case of circular channels, as outlined, the cylindrical form is advisable; in the case of a rectangular cross section in the burner channel, a cuboidal body is preferably suitable. The configuration which is particularly suitable in each case can be determined by the person skilled in the art.

The diameter of the bores to be made in the turbulence generators is typically from about 0.1 to 0.5 and preferably from 0.2 to 0.4 times the cylinder diameter, i.e. the external diameter of the turbulence generator.

In the process according to the invention, the gas undergoes the deflection outlined above as it flows through the bores in the turbulence generators. A swirl is thus imparted to the gas; a swirling flow forms. Thus, the deflection of the flowing medium here generates a marked radial and tangential velocity component at the exit from the burner. The high shear forces that jets exiting adjacently (i.e. from adjacent burner channels) exert on one another results in the formation of highly varying velocities. This advantageously allows the formation of an energetically highly intense, turbulent flow field in the combustion chamber, in which the reaction zone can form. The turbulence formed is characterized by flow conditions under which highly variable velocities in all three spatial directions are formed and, moreover, no macroscopic preference in circumferential direction can be discerned.

The inventive arrangement of the turbulence generators in the channels of the burner block gives rise to a novel and improved process regime which will be discussed in detail below. According to the invention, the reaction is stabilized here in another way. In addition to the use of stabilizing flames, the turbulence generator generates a high-intensity flow field in which the reaction zone can form. The type of flow field formed and the process regime advantageously have the effect that no recirculation of streams close to the burner block is observed here, which ultimately leads to the effect that no coke deposits on the burner block are observed here. In addition to the advantageous configuration of the turbulence field already outlined, the avoidance of the undesired recirculation of soot-containing gas streams at the burner block is also brought about by the inventive configuration of the positioning of the stabilizing flames. In contrast to conventional burners, the stabilizing flames are at a significant distance from the burner block; the distance is preferably, for instance, from 3 to 20 and more preferably from 4 to 15 times the diameter of a channel in the burner block. This distance is measured from the lower edge of the burner block, i.e. the point at which the gas stream leaves the channels in the direction of the combustion chamber and the point at which the auxiliary oxygen is introduced into the combustion chamber. Typically, the diameters of the channels in the burner block are, for instance, within a range from 17 to 27 mm and preferably from 20 to 23 mm. As a result of this positioning of the stabilizing flames, the flame is stabilized in the process according to the invention significantly further away from the burner block than in conventional burners. The particularly preferred positioning of the stabilizing flames in each case depends on the particular system and the specific existing process technology conditions. An appropriate variation can be carried out in the individual case by the person skilled in the art according to the existing reaction conditions. A simple shift of the stabilizing flames in conventional burners to a similar distance would not lead to success in a comparable manner, since the burner bores thereof are not provided at the exit with turbulence generators in accordance with the invention and thus no turbulent flow field is established downstream of the exit, in which the main flame is stabilized only by use of auxiliary oxygen and without the stabilizing effect of the recirculation at the burner exit bores.

The process according to the invention offers generation of high turbulence in the combustion chamber with minimal pressure drop. The pressure drop depends on the throughput and is from about 40 to 300 mbar at the design point of the reactor.

The turbulence generators, in terms of arrangement, preferably have an alternating direction of rotation (clockwise and counterclockwise). This advantageously allows a turbulent flow field to be formed in the combustion chamber without an integral resultant of the tangential velocity, which allows particularly effective mixing to be achieved.

Figure 2:
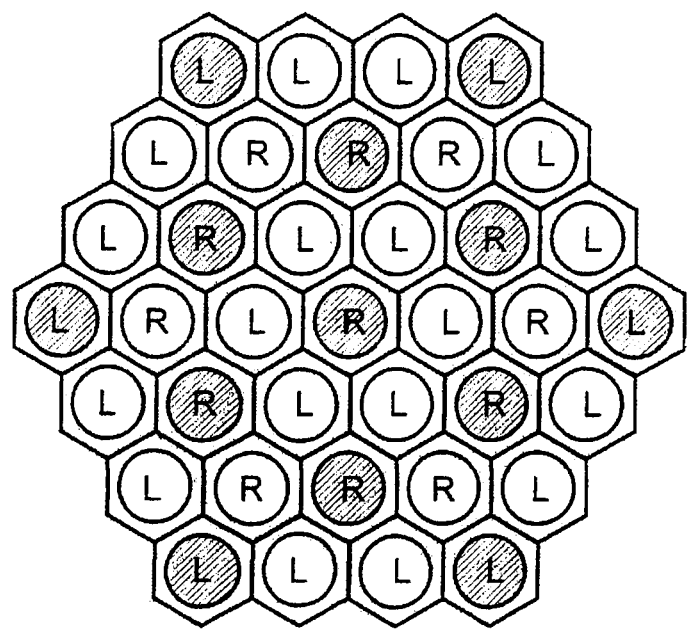
FIG. 2 shows an alternating arrangement of spiral rotations of adjacent turbulence generators according to one embodiment of the invention.

A preferred arrangement of the turbulence generators envisages that the directions of rotation are alternated in radial direction, but turbulence generators of the same design are used in peripheral direction. The arrangement of directions of rotation for the turbulence generators which conduct oxidant and fuel in the burner plate is shown in FIG. 2.

It is possible for turbulence generators to be disposed in all channels or only in some thereof.

The present invention further provides an apparatus suitable for the performance of the process according to the invention. This is explained in detail below by way of example with reference to FIG. 1.

By means of feeds (1) and (2), oxidant and fuel are supplied separately from one another through lines (3) provided with turbulence generators in the burner block. Only downstream of the turbulence generators, which are preferably manufactured from axial swirl generators, do oxidant and fuel come into contact, and are mixed in the intensive turbulent field. The length of the mixing chamber (4) is such that it is sufficient for sufficient homogenization of the mixture. Through the feeds (5), oxygen or a reaction assistant passes into the reaction chamber (6), where the reaction zone is stabilized.

FIG. 2 shows a preferred arrangement of the turbulence generators. "R" and "L" schematically denote turbulence generators of different direction of rotation ("R" rotation to the right, "L" rotation to the left). In peripheral direction, turbulence generators of the same direction of rotation are accordingly preferably present on a circular arc, while alternating directions of rotation are arranged in radial direction. Oxidant is introduced here into the lines identified with hatching in FIG. 2.

The process according to the invention enables an economically viable partial oxidation of hydrocarbons. It is more preferably suitable for the preparation of acetylene and synthesis gas in high yields. In contrast to processes in conventional burners, the process provides a partial oxidation without undesired coke deposition, which leads to impairment of the process. At the same time, the inventive method of stabilization of the flame in the burner, owing to the prevention of coke deposition by recirculation, provides an effective and economically viable reaction regime. At the same time, the advantages can be realized in a simple manner by the inventive flow technology configuration, thus preventing increased complexity, for example the periodic, mechanical cleaning of the burner.

EXAMPLE

Experimental measurements for the mixing were carried out in an inventive apparatus shown in FIG. 1. A reactor chamber with a diameter of 170 mm was provided with 37 bores of 25 mm. The gas leaving the bores was considered with a tangential velocity component with alternating direction of rotation at the flow outlet of the bores by the turbulence generators present in the lines. The turbulence generators featured four bores which covered an angle of 360° given a length of the cylinder of 5 cm.

The distribution of oxidant and fuel inlets was selected so as to give rise to a homogeneously distributed momentum flow density from the respective bores overall; for this purpose, an arrangement as shown in FIG. 2 was selected.

Figure 3:
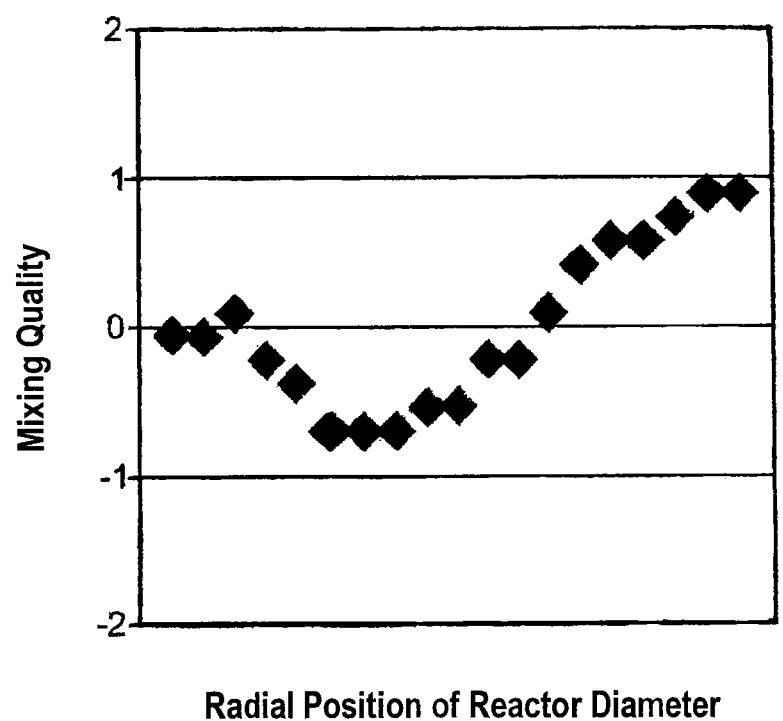
FIG. 3 shows a graph of reactant gas mixing quality over radial distance of the reactor.

Radial concentration measurements to determine the quality of the mixing of oxidant and fuel were carried out at the level of flame stabilization, i.e. at the exit of the mixing zone and transition into the reactor chamber. The distance between measurement point and the exit of the reaction media (number 7 in FIG. 1) was 8 bore diameters. The diagram in FIG. 3 shows the mixing quality determined over radial position (a determination was carried out over the entire reactor diameter of 170 mm). The diagram shows the percentage deviation of the actually determined mixture with regard to the fuel content (methane) as compared with ideal mixing. It can be seen that the deviation from ideal mixing is less than 1 percent in the inventive configuration; this embodiment thus enables effective process performance.

The invention claimed is:
1. A process for partial oxidation of a hydrocarbon, the process comprising:
    separately feeding a stream comprising the hydrocarbon and a stream comprising oxygen
    through channels of a burner block of a reactor, in each case one or more spatially separate lines to a reaction zone, wherein at least one of the spatially separate feed lines comprises an interior turbulence generator, the turbulence generator comprises a cylindrical body with a bore passing from one circular face to the opposite circular face in a spiral path about a longitudinal axis of the cylindrical body, and as a result of imposed deflection of the feed stream in the turbulence generator, the feed stream exiting from the turbulence generator has a tangential flow component and a turbulent flow field forms, is obtained downstream of the turbulence generator, wherein the turbulence generator blocks 10 to 70% of a percentage area of a flow cross section of the feed line, and a curved deflection in a circumference angle of the spiral bore is from 45° to 360°;

mixing the streams in a mixing zone with the turbulent flow; and then converting the hydrocarbon to at least one product in a reaction zone downstream of the mixing zone.

2. The process according to claim 1, wherein the product comprises acetylene and synthesis gas.

3. The process according to claim 2, wherein a mixing zone is formed downstream of the turbulence generators of the burner block by disposing a stabilizing flame at a distance of from 6 times to 15 times a channel diameter from a lower edge of the burner block.

4. The process according to claim 1, wherein all the spatially separate feed lines comprise a turbulence generator.

5. The process according to claim 4, wherein a mixing zone is formed downstream of the turbulence generators of the burner block by disposing a stabilizing flame at a distance of from 6 times to 15 times a channel diameter from a lower edge of the burner block.

6. The process according to claim 1, wherein the turbulence generators are arranged such that the spiral bore of alternating channels turn in opposite direction and, as a stream flows through the channels, based on adjacent channels, an alternating direction of rotation is formed.

7. The process according to claim 6, wherein a mixing zone is formed downstream of the turbulence generators of the burner block by disposing a stabilizing flame at a distance of from 6 times to 15 times a channel diameter from a lower edge of the burner block.

8. The process according to claim 1, wherein a mixing zone is formed downstream of the turbulence generators of the burner block by disposing a stabilizing flame at a distance of from 6 times to 15 times a channel diameter from a lower edge of the burner block.

9. An apparatus for performing the process according to claim 1 which comprises a reactor for acetylene preparation, said reactor comprising, based on the flow direction of feed stocks from upstream of the reactor:

a burner block;
a mixing zone; and
a reaction zone;
wherein separate feed lines conduct the reactants through the burner block to the mixing zone, one or more of the separate feed lines comprises a turbulence generator, the turbulence generator blocks from 10 to 70% of an area of the flow cross section of the feed line, the turbulence generator comprises a cylindrical body with a bore passing from one circular face to the opposite circular face in a spiral path about a longitudinal axis of the cylindrical body, and a curved deflection in a circumference angle of the spiral bore is from 45° to 360°.

10. The apparatus according to claim 9, wherein a slope of the spiral bore relative to the longitudinal axis is from 40° to 80°.

11. The apparatus according to claim 9, wherein all the feed lines comprise a turbulence generator.

12. The apparatus according to claim 11, wherein a spiral rotation of adjacent turbulence generators alternates between clockwise and counterclockwise rotation.

13. The apparatus according to claim 11, wherein the turbulence generators are disposed in the lines such that, as a stream flows through channels, based on adjacent channels, an alternating direction of rotation is formed.

14. The apparatus according to claim 9, wherein a spiral rotation of adjacent turbulence generators alternates between clockwise and counterclockwise rotation.

15. The apparatus according to claim 9, further comprising: a stabilizing flame at a distance of from 6 times to 15 times a channel diameter from a lower edge of the burner block.

* * * * *